US008470807B2

(12) United States Patent
Tanaka et al.

(10) Patent No.: US 8,470,807 B2
(45) Date of Patent: Jun. 25, 2013

(54) ANTIOXIDANT

(75) Inventors: Miyuki Tanaka, Zama (JP); Kouji Nomaguchi, Zama (JP); Tatsuya Ehara, Zama (JP)

(73) Assignee: Morinaga Milk Industry Co., Ltd., Minato-ku, Tokyo (JP)

( * ) Notice: Subject to any disclaimer, the term of this patent is extended or adjusted under 35 U.S.C. 154(b) by 153 days.

(21) Appl. No.: 13/127,698

(22) PCT Filed: Nov. 18, 2009

(86) PCT No.: PCT/JP2009/069563
§ 371 (c)(1),
(2), (4) Date: May 4, 2011

(87) PCT Pub. No.: WO2010/058795
PCT Pub. Date: May 27, 2010

(65) Prior Publication Data
US 2011/0212931 A1 Sep. 1, 2011

(30) Foreign Application Priority Data

Nov. 19, 2008 (JP) ................................ 2008-295488

(51) Int. Cl.
*A61K 31/56* (2006.01)

(52) U.S. Cl.
USPC ......................................................... 514/182

(58) Field of Classification Search
USPC ......................................................... 514/182
See application file for complete search history.

(56) References Cited

U.S. PATENT DOCUMENTS

| | | | |
|---|---|---|---|
| 4,748,161 | A | 5/1988 | Kimura et al. |
| 6,087,345 | A | 7/2000 | Ohta et al. |
| 2006/0045928 | A1* | 3/2006 | Oshiro ........................ 424/756 |
| 2007/0032463 | A1* | 2/2007 | Higuchi et al. ............... 514/169 |
| 2007/0196435 | A1* | 8/2007 | Higuchi et al. ............... 424/439 |
| 2008/0255077 | A1 | 10/2008 | Tanaka et al. |
| 2009/0004307 | A1 | 1/2009 | Tanaka et al. |
| 2009/0054354 | A1 | 2/2009 | Tanaka et al. |
| 2009/0075913 | A1 | 3/2009 | Higuchi et al. |
| 2009/0093450 | A1 | 4/2009 | Tanaka et al. |
| 2009/0131388 | A1 | 5/2009 | Tanaka et al. |
| 2009/0312275 | A1 | 12/2009 | Tanaka et al. |
| 2010/0035851 | A1 | 2/2010 | Tanaka et al. |
| 2010/0240632 | A1 | 9/2010 | Higuchi et al. |
| 2010/0286104 | A1 | 11/2010 | Tanaka et al. |

FOREIGN PATENT DOCUMENTS

| | | |
|---|---|---|
| EP | 1 795 200 | 6/2007 |
| JP | 57-018617 | 1/1982 |
| JP | 60-258119 | 12/1985 |
| JP | 05-051388 | 3/1993 |
| JP | 06-298645 | 10/1994 |
| JP | 11 075770 | 3/1999 |
| JP | 2000-198726 | 7/2000 |
| JP | 2004-149729 | 5/2004 |
| JP | 2005-029490 | 2/2005 |
| JP | 2006-008719 | 1/2006 |
| JP | 2006-160668 | 6/2006 |
| JP | 2007-016077 | 1/2007 |
| WO | WO 2005/094838 | 10/2005 |
| WO | WO 2006/035525 | 4/2006 |
| WO | WO 2007/043294 | 4/2007 |
| WO | WO 2007/043305 | 4/2007 |
| WO | WO 2007/043306 | 4/2007 |
| WO | WO 2007/060911 | 5/2007 |
| WO | WO 2007/118605 | 10/2007 |
| WO | WO 2008/028097 | 3/2008 |

OTHER PUBLICATIONS

Calabresi P and Chabner BA, "Section IX Chemotherapy of Neoplastic Diseases—Introduction," Goodman & Gilman's The Pharmacological Basis of Therapeutics 10th ed., 2001, Hardman JG, Limbird LE, and Gilman AG, Eds, McGraw-Hill, New York 2001, 1381-1388 (pp. 1381, 1383-1385, and 1388 provided).*
Osawa T, Kato Y. Protective role of antioxidative food factors in oxidative stress caused by hyperglycemia. Ann N Y Acad Sci. Jun. 2005;1043:440-51.*
Tanimoto, et al. "Koshiketsu Shiketsusho Chiryoyaku no Kiso -Kiso: Koshikessho Chiryoyaku no Kenkyu Kaihatsu-," *Folia Pharmacologica Japonica*, vol. 129, pp. 267-270, 2007.
International Search Report dated Mar. 2, 2010 and issued to international application No. PCT/JP2009/069563.
Rumyantsev, et al. "The Chemical Basis of Life," Moscow, 2007, pp. 432-434. Partial.
Office Action dated Sep. 6, 2012 issued to the corresponding Russian Patent Application No. 2011124905/04.
Kunitomo, Masaru, "Oxidative Stress and Atherosclerosis," *Yakugaku Zasshi*, vol. 127, No. 12, pp. 1997-2014, 2007.
Maeura, et al. "Dose-dependent Reduction of N-2-Fluorenylacetamide-induced Liver Cancer and Enhancement of Bladder Cancer in Rats by Butylated Hydroxytoluene," *Cancer Research*, vol. 44, pp. 1604-1610, Apr. 1984.
International Preliminary Report on Patentability dated Jun. 30, 2011 issued to international application No. PCT/JP2009/069563.
Abidi, "Chromatographic Analysis of Plant Sterols in Foods and Vegetable Oils," Journal of Chromatography A, vol. 935, pp. 173-201, 2001.
Extended European Search Report dated Oct. 19, 2012 issued to European patent application No. 09827576.1.
Kim et al., "Melatonin reduces X-ray irradiation-induced oxidative damages in cultured human skin fibroblasts," *Journal of Dermatological Science*, vol. 26, pp. 194-200 (2001).
Lomnitski et al., "In Vitro and In Vivo Effects of β-Carotene on Rat Epidermal Lipoxygenases," *Internal. J. Vit. Nutr. Res.*, vol. 67, pp. 407-414 (1997).
Thiele, et al., "In Vivo Exposure to Ozone Depletes Vitamins C and E and Induces Lipid Peroxidation in Epidermal Layers of Murine Skin," *Free Radical Biology & Medicine*, vol. 23(3), pp. 385-391 (1997).

* cited by examiner

*Primary Examiner* — Paul Zarek
(74) *Attorney, Agent, or Firm* — Knobbe, Martens, Olson & Bear LLP

(57) ABSTRACT

Provided is an antioxidant which is highly safe, inhibits oxidation of a biological component, in particular, a lipid, and may be used as a drug, food or drink, a food additive, an external preparation for skin, or the like. The antioxidant contains a compound selected from a cyclolanostane compound and a lophenol compound as an active ingredient.

8 Claims, No Drawings

ANTIOXIDANT

CROSS-REFERENCE TO RELATED APPLICATIONS

This application is the U.S. National Phase under 35 U.S.C. §371 of International Application PCT/JP2009/069563, filed Nov. 18, 2009, which was published in a non-English language, which claims priority to JP Patent Application No. 2008-295488, filed Nov. 19, 2008.

TECHNICAL FIELD

The present invention relates to an antioxidant which can be used as a drug, food or drink, a food additive, an external preparation for skin, or the like.

BACKGROUND ART

"Oxidative stress" is defined as a state where a living body has oxidative tendency as a result of an imbalance between production of reactive oxygen species (ROS) and antioxidative defense mechanisms in a living body. That is, excessive production of the ROS or a decrease in antioxidative ability leads to the oxidative stress.

The ROS oxidizes a lipid, in particular, a low-density lipoprotein (LDL) of a phopholipid to form a lipid peroxide and oxidized LDL, and oxidatively denatures and deactivates a protein to cause an oxidative damage of DNA. It is therefore said that the oxidative stress is involved in development of many diseases such as arteriosclerosis, cancer, various lifestyle-related diseases, Alzheimer's disease, and Parkinson's disease and promotes aging, through damages of cells and tissues and impairment of vital functions (for example, see Non Patent Document 1).

Further, the skin is in a state in which the ROS is easily produced by an irritation of an environmental factor such as an ultraviolet ray. The ROS in the skin causes, for example, destruction of a body tissue such as collagen to damage cells, resulting in skin symptoms such as wrinkles, a decrease in elasticity, an inflammation, and pigmentation. Also, the ROS is known to oxidize proteins and lipids in the scalp to cause hair loss (for example, Patent Documents 1 and 2).

Meanwhile, if the concentration of the lipid peroxide increases in blood, the lipid peroxide itself or an oxidative decomposition product thereof is known to act directly on nucleic acids and proteins to cause angiopathy, hepatic dysfunction, cataract, or the like. Moreover, the lipid peroxide causes injury of vascular endothelial cells, enhancement of platelet aggregation, formation of foam cells, or the like, and hence is considered to be a cause of arteriosclerosis.

For example, it is known that a primary lesion of arteriosclerosis is caused by an oxidized low-density lipoprotein (LDL), and that the easiest method of detecting oxidation of LDL is measurement of lipid peroxide (for example, Non Patent Document 2).

As antioxidants from natural products, vitamin E, vitamin C, a neutral fraction of an extract of a *Helichrysum* plant (for example, Patent Document 1), an extract of *Chimaphila umbellata* (for example, Patent Document 2), and the like are known.

In particular, known drugs or the like for inhibiting formation of a lipid peroxide in a living body include an agent containing sesamin and/or episesamin as an active ingredient (for example, Patent Document 3), an agent characterized by containing fructo-oligosaccharide (for example, Patent Document 4), an agent containing, as an active ingredient, an extract obtained by extraction from leaves of *Psidium guajava L.* (for example, Patent Document 5), an agent for inhibiting formation of a lipid peroxide characterized by containing an extract of a plant native to Mexico with a scientific name of *Gnaphalium semiamlexicaule* (for example, Patent Document 6), an agent containing astaxanthin and/or an ester thereof (for example, Patent Document 7), and an agent containing both an *Apocynum venetum L.* extract and a vitamin C compound (for example, Patent Document 8).

Further, Patent Document 9 discloses an application, as an agent for preventing and treating hyperlipemia, of γ-orizanol, which is a mixture of compounds obtained by independently binding campesterol, β-sitosterol, cycloartenol, 24-methylene cycloartanol, and cyclobranol to ferulic acid ester. Patent Document 10 discloses that single administration of any one of cycloartenol and 24-methylcycloartenol leads to a decrease in cholesterol in blood plasma and a decrease in high-density lipoprotein cholesterol (HDL-C) and leads to no significant change in TG, PL, and LPO.

Moreover, antioxidants such as 3,5-tert-butyl-4-hydroxytoluene (BHT) and 2,3-tert-butyl-hydroxyanisole (BHA) have been developed to inhibit oxidation of a lipid or the like. However, such antioxidants may be carcinogens (for example, Non Patent Document 3) and are difficult to use safely.

Under such circumstances, development of a novel antioxidative substance which can be used safely and has no side effects has been desired.

Note that, an agent for improving hyperglycemia, an agent for improving pancreatic function, an agent for improving insulin resistance, and an agent for inhibiting visceral fat accumulation, each of which contains a cyclolanostane compound such as 9,19-cyclolanostane-3-ol or 24-methylene-9,19-cyclolanostane-3-ol, or a lophenol compound such as methylcholest-7-en-3-ol, 4-methylergost-7-en-3-ol, or 4-methylstigmast-7-en-3-ol as an active ingredient, are known (as in Patent Documents 11 to 13, Patent Documents 14 and 15, Patent Documents 16 and 17, and Patent Document 18, respectively).

PRIOR ART DOCUMENTS

Patent Document

[Patent Document 1] JP-A-2007-016077
[Patent Document 2] JP-A-2004-149729
[Patent Document 3] JP-A-5-51388
[Patent Document 4] JP-A-8-325157
[Patent Document 5] JP 11-75770
[Patent Document 6] JP-A-2000-198726
[Patent Document 7] JP-A-2006-8719
[Patent Document 8] JP-A-2006-160668
[Patent Document 9] JP 06-298645 A
[Patent Document 10] JP 05-33713 B2
[Patent Document 11] WO 2007/060911 A1
[Patent Document 12] WO 2006/035525 A1
[Patent Document 13] WO 2005/094838 A1
[Patent Document 14] WO 2006/123466 A1
[Patent Document 15] WO 2006/123465 A1
[Patent Document 16] WO 2007/043306 A1
[Patent Document 17] WO 2007/043305 A1
[Patent Document 18] WO 2007/043294 A1

Non Patent Document

[Non Patent Document 1] YAKUGAKU ZASSHI, 127(12) 2007, 1997-2014

[Non Patent Document 2] "Oxidative Stress Navigator," Masahiko Kurabayashi, Ed., Medical Review Co., Ltd., 2005, 192-193

[Non Patent Document 3] Cancer Research, 44, 1984, 1604-1610

SUMMARY OF INVENTION

An object of the present invention is to provide an antioxidant which is highly safe, inhibits oxidation of a biological component, in particular, a lipid, and can be used as a drug, food or drink, a food additive, an external preparation for skin, or the like. In particular, an object of the present invention is to provide a drug, food or drink, or the like for inhibiting formation of a lipid peroxide, which effectively inhibits formation of a lipid peroxide in blood.

The first invention for solving the above-mentioned problem is an antioxidant containing a compound selected from a cyclolanostane compound and a lophenol compound as an active ingredient (hereinafter, referred to as "antioxidant of the present invention") and includes the following preferred embodiments (1) to (9):

(1) containing the cyclolanostane compound and the lophenol compound at the following mass ratio;
cyclolanostane compound:lophenol compound=6.3:2.7 to 5.1:4.9;

(2) containing the compound selected from the cyclolanostane compound and the lophenol compound at a concentration of at least 0.0001% by mass;

(3) the cyclolanostane compound being selected from 9,19-cyclolanostan-3-ol and 24-methylene-9,19-cyclolanostan-3-ol;

(4) the lophenol compound being selected from 4-methylcholest-7-en-3-ol, 4-methylergost-7-en-3-ol, and 4-methylstigmast-7-en-3-ol;

(5) being used for inhibiting oxidation of a lipid;

(6) being used for inhibiting formation of a lipid peroxide;

(7) being an external preparation for skin;

(8) consisting of food or drink containing the compound selected from the cyclolanostane compound and the lophenol compound; and (9) containing an emulsifier.

The second invention for solving the above-mentioned problem is a method of manufacturing an antioxidant which includes mixing the compound selected from the cyclolanostane compound and the lophenol compound as an active ingredient. Preferred embodiments of the compound are the same as those of the first invention.

The first invention includes an embodiment of a drug for inhibiting formation of a lipid peroxide which contains the compound selected from the cyclolanostane compound and the lophenol compound as an active ingredient. The embodiment includes the following preferred embodiments (10) to (13):

(10) containing the cyclolanostane compound and the lophenol compound at the following mass ratio:
cyclolanostane compound:lophenol compound=6.3:2.7 to 5.1:4.9;

(11) containing the compound selected from the cyclolanostane compound and the lophenol compound at a concentration of at least 0.0001% by mass;

(12) the cyclolanostane compound being selected from 9,19-cyclolanostan-3-ol and 24-methylene-9,19-cyclolanostan-3-ol; and

(13) the lophenol compound being selected from 4-methylcholest-7-en-3-ol, 4-methylergost-7-en-3-ol, and 4-methylstigmast-7-en-3-ol.

The second invention includes an embodiment of a method of manufacturing a drug for inhibiting formation of a lipid peroxide, the method including mixing the compound selected from the cyclolanostane compound and the lophenol compound as an active ingredient. Preferred embodiments of the compound in this embodiment are the same as those described above.

The first invention includes an embodiment of food or drink for inhibiting formation of a lipid peroxide which contains the compound selected from the cyclolanostane compound and the lophenol compound as an active ingredient. The embodiment includes the following preferred embodiments (14) to (20):

(14) containing the cyclolanostane compound and the lophenol compound at the following mass ratio:
cyclolanostane compound:lophenol compound=6.3:2.7 to 5.1:4.9;

(15) containing the compound selected from the cyclolanostane compound and the lophenol compound at a concentration of at least 0.0001% by mass;

(16) the cyclolanostane compound being selected from 9,19-cyclolanostan-3-ol and 24-methylene-9,19-cyclolanostan-3-ol;

(17) the lophenol compound being selected from 4-methylcholest-7-en-3-ol, 4-methylergost-7-en-3-ol, and 4-methylstigmast-7-en-3-ol;

(18) further containing an emulsifier;

(19) containing a fat and oil; and

(20) being a functional food or drink.

The second invention includes an embodiment of a method of manufacturing food or drink for inhibiting formation of a lipid peroxide which includes mixing the compound selected from the cyclolanostane compound and the lophenol compound as an active ingredient. Preferred embodiments of the compound in this embodiment are the same as those described above.

The first invention includes an embodiment of a food additive for inhibiting formation of a lipid peroxide which contains the compound selected from the cyclolanostane compound and the lophenol compound as an active ingredient. The embodiment includes the following preferred embodiments (21) to (25):

(21) further containing an emulsifier;

(22) containing the cyclolanostane compound and the lophenol compound at the following mass ratio:
cyclolanostane compound:lophenol compound=6.3:2.7 to 5.1:4.9;

(23) containing the compound selected from the cyclolanostane compound and the lophenol compound at a concentration of at least 0.001% by mass;

(24) the cyclolanostane compound being selected from 9,19-cyclolanostan-3-ol and 24-methylene-9,19-cyclolanostan-3-ol; and

(25) the lophenol compound being selected from 4-methylcholest-7-en-3-ol, 4-methylergost-7-en-3-ol, and 4-methylstigmast-7-en-3-ol.

The second invention includes an embodiment of a method of manufacturing a food additive for inhibiting formation of a lipid peroxide, the method including mixing the compound selected from the cyclolanostane compound and the lophenol compound as an active ingredient. Preferred embodiments of the compound in this embodiment are the same as those described above. An embodiment of mixing an emulsifier is also preferred.

Further, the third invention for solving the above-mentioned problem is use of the compound selected from the cyclolanostane compound and the lophenol compound in the manufacture of an antioxidant. Preferred embodiments of the compound are the same as those of the first invention.

Further, the third invention includes the following embodiments:

(26) use of a composition containing the cyclolanostane compound and the lophenol compound at the following mass ratio in the manufacture of an antioxidant:

cyclolanostane compound:lophenol compound=6.3:2.7 to 5.1:4.9; and

(27) use of a composition containing the compound selected from the cyclolanostane compound and the lophenol compound at a concentration of at least 0.0001% by mass in the manufacture of an antioxidant.

The third invention includes an embodiment of use of the compound selected from the cyclolanostane compound and the lophenol compound in the manufacture of a drug for inhibiting formation of a lipid peroxide. Preferred embodiments of the compound are the same as those of the first invention.

Further, the embodiment includes the following embodiments:

(28) use of a composition containing the cyclolanostane compound and the lophenol compound at the following mass ratio in the manufacture of a drug for inhibiting formation of a lipid peroxide:

cyclolanostane compound:lophenol compound=6.3:2.7 to 5.1:4.9; and

(29) use of a composition containing the compound selected from the cyclolanostane compound and the lophenol compound at a concentration of at least 0.0001% by mass in the manufacture of a drug for inhibiting formation of a lipid peroxide.

The third invention includes an embodiment of use of the compound selected from the cyclolanostane compound and the lophenol compound in the manufacture of food or drink for inhibiting formation of a lipid peroxide. Preferred embodiments of the compound in this embodiment are the same as those of the first invention.

Further, the embodiment includes the following embodiments:

(30) use of a composition containing the cyclolanostane compound and the lophenol compound at the following mass ratio in the manufacture of food or drink for inhibiting formation of a lipid peroxide:

cyclolanostane compound:lophenol compound=6.3:2.7 to 5.1:4.9; and

(31) use of a composition containing the compound selected from the cyclolanostane compound and the lophenol compound at a concentration of at least 0.0001% by mass in the manufacture of food or drink for inhibiting formation of a lipid peroxide.

The third invention also includes an embodiment of use of the compound selected from the cyclolanostane compound and the lophenol compound in the manufacture of a food additive for inhibiting formation of a lipid peroxide. Preferred embodiments of the compound are the same as those of the first invention.

Further, the embodiment includes the following embodiments:

(32) use of a composition containing the cyclolanostane compound and the lophenol compound at the following mass ratio in the manufacture of a food additive for inhibiting formation of a lipid peroxide:

cyclolanostane compound:lophenol compound=6.3:2.7 to 5.1:4.9; and

(33) use of a composition containing the compound selected from the cyclolanostane compound and the lophenol compound at a concentration of at least 0.001% by mass in the manufacture of a food additive for inhibiting formation of a lipid peroxide.

Further, the fourth invention for solving the above-mentioned problem is the compound which is selected from the cyclolanostane compound and the lophenol compound, for use in antioxidation. Preferred embodiments of the compound are the same as those of the first invention. The above-mentioned compound is preferably for use in inhibiting oxidation of a lipid and is preferably for use in inhibiting formation of a lipid peroxide.

The fourth invention includes an embodiment of a composition for use in inhibiting formation of a lipid peroxide, which contains the compound selected from the cyclolanostane compound and the lophenol compound. Preferred embodiments of the composition include the following embodiments:

(34) a composition containing the compound selected from the cyclolanostane compound and the lophenol compound, and an emulsifier;

(35) a composition containing the cyclolanostane compound and the lophenol compound at the following mass ratio:

cyclolanostane compound:lophenol compound=6.3:2.7 to 5.1:4.9; and

(36) a composition containing the compound selected from the cyclolanostane compound and the lophenol compound at a concentration of at least 0.0001% by mass.

Further, the fifth invention for solving the above-mentioned problem is a method of treating or preventing a disease or symptom attributed to oxidation, the method including administering the compound selected from the cyclolanostane compound and the lophenol compound to a subject who requires antioxidation. Preferred embodiments of the compound are the same as those of the first invention.

Further, the fifth invention includes the following preferred embodiments (37) to (39):

(37) administering the cyclolanostane compound and the lophenol compound at the following mass ratio:

cyclolanostane compound:lophenol compound=6.3:2.7 to 5.1:4.9;

(38) administering a composition containing the cyclolanostane compound and the lophenol compound at the mass ratio described above; and

(39) administering a composition containing the compound selected from the cyclolanostane compound and the lophenol compound at a concentration of at least 0.0001% by mass.

Further, the sixth invention for solving the above-mentioned problem is a method of imparting an antioxidative activity to food or drink, the method including adding the compound selected from the cyclolanostane compound and the lophenol compound to the food or drink so that the total concentration of the compound in the food or drink is at least 0.0001% by mass. Preferred embodiments of the compound are the same as those of the first invention.

Further, the seventh invention for solving the above-mentioned problem is a method of enhancing an antioxidative activity of food or drink containing the compound selected from the cyclolanostane compound and the lophenol compound, the method including adding the compound selected from the cyclolanostane compound and the lophenol compound to the food or drink so that the total concentration of the compound in the food or drink is at least 0.0001% by mass. Preferred embodiments of the compound are the same as those of the first invention.

The antioxidant of the present invention may be used in various forms including a drug, food or drink, a food additive, and an external preparation for skin, and inhibits oxidation of a biological component, in particular, oxidation of a lipid.

The drug of the present invention can be administered safely and effectively inhibits oxidation of a biological component, in particular, formation of a lipid peroxide in blood. Further, the food or drink of the present invention can be ingested safely and effectively inhibits oxidation of a biological component, in particular, formation of a lipid peroxide in blood. In addition, the food additive of the present invention is suitable for manufacture of the above-mentioned food or drink or for prevention of oxidation of a component in food or drink. Moreover, the external preparation for skin of the present invention can be applied safely and effectively inhibits oxidation of a skin component, in particular, formation of a lipid peroxide in the skin.

Further, the active ingredient in the antioxidant of the present invention, the cyclolanostane compound or the lophenol compound, can be manufactured by chemical synthesis, and according to the manufacture method of the invention of the present application, the antioxidant of the present invention can be easily manufactured. In addition, the active ingredient in the antioxidant of the present invention is known to be safe from the dietary experiences and can be easily manufactured from a plant of family Liliaceae which is easily available, for example, a plant such as *Aloe barbadensis* Miller. Therefore, according to the manufacture method of the invention of the present application, the antioxidant of the present invention can be easily manufactured.

DESCRIPTION OF EMBODIMENTS

Hereinafter, preferred embodiments of the present invention are described in detail. However, the present invention is not limited to the following preferred embodiments and any modification may be made within the scope of the present invention. Note that, in this description, all percentages are expressed as mass percentage unless otherwise specified.

The antioxidant of the present invention contains a compound selected from a cyclolanostane compound and a lophenol compound as an active ingredient.

[Cyclolanostane Compound]

The cyclolanostane compound (compound having a cyclolanostane skeleton) is represented by the following general formula (1).

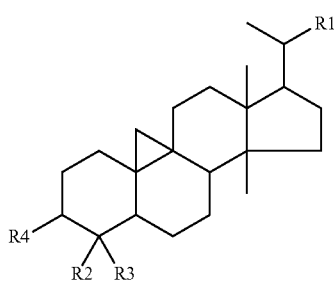

(1)

In the general formula (1), R1 represents an alkyl group or an alkenyl group including one or two double bonds, which is straight or branched chain having 6 to 8 carbon atoms, or a substituted alkyl or alkenyl group obtained by substituting one or two hydrogen atoms in the above-described alkyl and alkenyl groups for a hydroxyl group and/or a carbonyl group; R2 and R3 each independently represent a hydrogen atom or a methyl group; and R4 forms C=O with a carbon atom constituting a ring or represents any one of the following formulae.

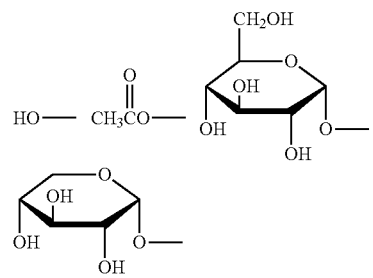

In the general formula (1), R1 preferably represents any one of groups represented by the following formulae.

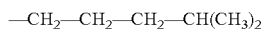

—CH$_2$—CH$_2$—CH$_2$—CH(CH$_3$)$_2$

—CH$_2$—CH$_2$—CHRa—C(CH$_3$)$_2$Rb (wherein Ra is a hydrogen atom, a hydroxyl group, or a methyl group; and Rb is a hydrogen atom or a hydroxyl group)

—CH$_2$—CH$_2$—CH(CH$_2$CH$_3$)—CH(CH$_3$)$_2$

—CH$_2$—CH$_2$—CHRc-C(CH$_3$)=CH$_2$ (wherein Rc is a hydrogen atom, a hydroxyl group, or a methyl group)

—CH$_2$—CH$_2$—C(=O)—C(CH$_3$)—CH$_2$

—CH$_2$—CH$_2$—C(=CH$_2$)—CH(CH$_3$)$_2$

—CH$_2$—CH$_2$—CH=C(CH$_3$)$_2$

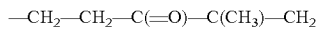

—CH$_2$—CH=C(CH$_3$)—CH(CH$_3$)$_2$

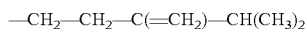

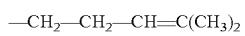

—CH$_2$—CH$_2$—C(=CHCH$_3$)—CH(CH$_3$)$_2$

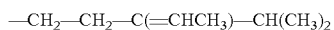

Preferred examples of the cyclolanostane compound include 9,19-cyclolanostan-3-ol and 24-methylene-9,19-cyclolanostan-3-ol.

The compounds have structures represented by the following formulae (2) and (3), respectively.

Formula (2): 9,19-cyclolanostan-3-ol

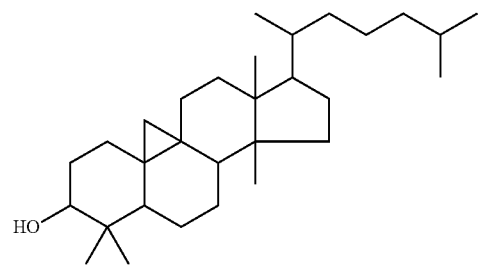

-continued

Formula (3): 24-methylene-9,19-cyclolanostan-3-ol

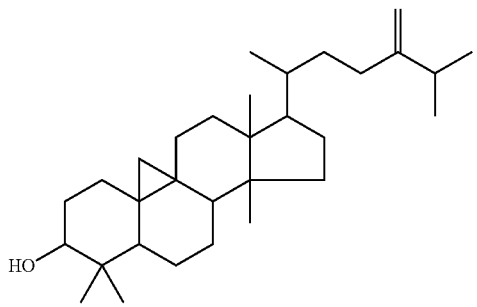

The cyclolanostane compound may be manufactured chemically according to a known manufacture method. For example, 24-methylene-9,19-cyclolanostan-3-ol (trivial name: 24-methylene cycloartanol) represented by the formula (3) can be manufactured by a method disclosed in JP 57-018617 A. Further, the cyclolanostane compound can be manufactured by a method disclosed in JP 2003-277269 A using, as a starting material, a hydrolysate of cycloartenol ferulate (formula (4)) from γ-orizanol.

Formula (4): Cycloartenol ferulate

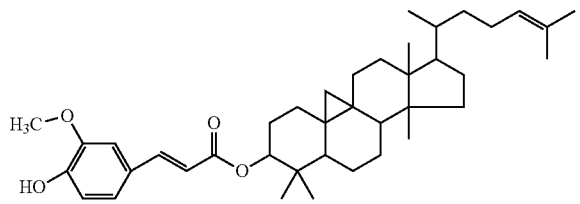

The cyclolanostane compound is known to be contained in a plant belonging to family Liliaceae, family Leguminosae, family Gramineae, family Solanaceae, or family Musaceae (see [Phytochemistry, USA, 1977, vol. 16, pp. 140-141], [Handbook of phytochemical constituents of GRAS herbs and other economic plants, 1992, USA, CRC Press], or [Hager's Handbuch der Pharmazeutischen Praxis, vol. 2-6, 1969-1979, Germany, Springer-Verlag, Berlin]). Therefore, the compound may be extracted from such plants by a method such as organic solvent extraction or hot water extraction.

Further, the cyclolanostane compound may be manufactured biologically using a microorganism or the like. Alternatively, the compound may be manufactured by using an enzyme derived from a microorganism.

The molecular weight, structure, and the like of the compound manufactured as above may be determined or confirmed by, for example, mass spectrometry (MS) and nuclear magnetic resonance spectrometry (NMR).

Further, the cyclolanostane compound may be a pharmaceutically acceptable salt. The pharmaceutically acceptable salt includes both a metal salt (inorganic salt) and an organic salt. Examples thereof include salts described in Remington's Pharmaceutical Sciences, 17th edition, 1985, p. 1418.

Specific examples of the salt include, but are not limited to: inorganic acid salts such as a hydrochloride, a sulfate, a phosphate, a diphosphate, a hydrobromide, and a sulfate; and organic acid salts such as a malate, a maleate, a fumarate, a tartrate, a succinate, a citrate, an acetate, a lactate, a methanesulfonate, a p-toluenesulfonate, a pamoate, a salicylate, and a stearate.

Meanwhile, the salt may be a salt with a metal such as sodium, potassium, calcium, magnesium, or aluminum, or a salt with an amino acid such as lysine. Moreover, there may also be used a solvate such as a hydrate of the above-mentioned compound or the pharmaceutically acceptable salt thereof.

[Lophenol Compound]

The lophenol compound (compound having a lophenol skeleton) is represented by the following general formula (5).

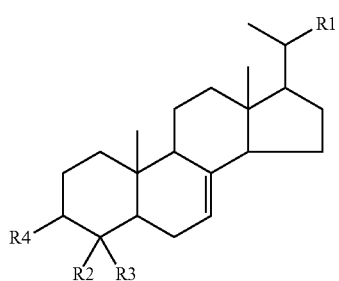

(5)

In the general formula (5), R1 represents an alkyl group or an alkenyl group including one or two double bonds, which is straight or branched chain having 5 to 16 carbon atoms. The alkyl or alkenyl group may be a substituted alkyl or alkenyl group obtained by substituting at least one hydrogen atom for a hydroxyl group and/or a carbonyl group. R2 and R3 each independently represents a hydrogen atom, an alkyl group or a substituted alkyl group having 1 to 3 carbon atoms; and R4 forms C=O with a carbon atom constituting a ring or represents —OH or —OCOCH$_3$. The alkyl group having 1 to 3 carbon atoms is preferably a methyl group, an ethyl group, or the like, particularly preferably a methyl group.

In the general formula (5), R1 preferably represents any one of groups represented by the following formulae.

—CH$_2$—CH$_2$—CH(—CH$_2$—CH$_3$)—CH(CH$_3$)$_2$

—CH$_2$—CH$_2$—CH=C(CH$_3$)$_2$

—CH$_2$—CH=C(CH$_3$)—CH(CH$_3$)$_2$

—CH$_2$—CH$_2$—C(=CH—CH$_3$)—CH(CH$_3$)$_2$

—CH$_2$—CH$_2$—CH(Ra)=C(CH$_3$)Rb (wherein Ra and Rb are any of —H, —OH, or —CH$_3$)

—CH$_2$—CH$_2$—CH(Rc)-CH(CH$_3$)Rd (wherein Rc and Rd are any of —H, —OH, or —CH$_3$)

Preferred examples of the lophenol compound include 4-methylcholest-7-en-3-ol, 4-methylergost-7-en-3-ol, and 4-methylstigmast-7-en-3-ol.

The compounds have structures represented by the following formulae (6) to (8), respectively.

Formula (6): 4-methylcholest-7-en-3-ol

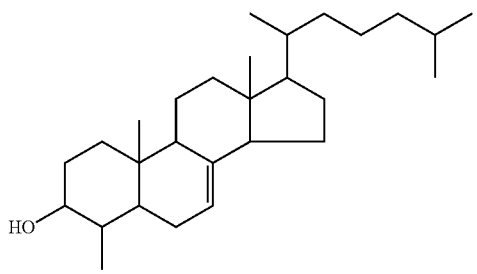

Formula (7): 4-methylergost-7-en-3-ol

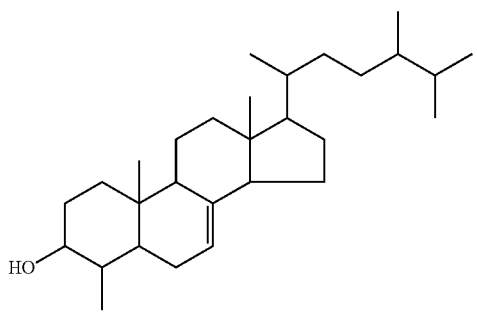

Formula (8): 4-methylstigmast-7-en-3-ol

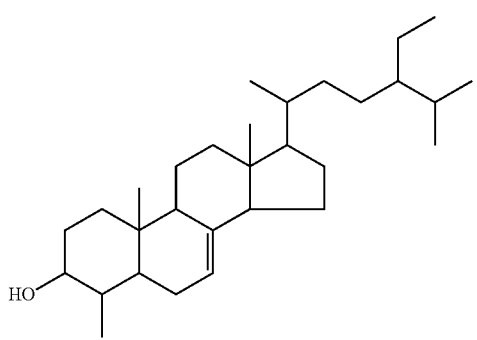

The lophenol compound is known to be contained in plants like the cyclolanostane compound and may be manufactured using a plant as a raw material according to a known method of manufacturing a lophenol (for example, see JP 3905913 B). Further, the lophenol compound may be synthesized according to, for example, the supplement data described in Vitali Matyash et al., PLOS BIOLOGY, Volume 2, Issue 10, e280, 2004.

The molecular weight, structure, and the like of the compound manufactured as above may be determined or confirmed by, for example, mass spectrometry (MS) and nuclear magnetic resonance spectrometry (NMR).

Further, the lophenol compound may be a pharmaceutically acceptable salt. The pharmaceutically acceptable salt includes the same salts as those in the case of the cyclolanostane compound.

[Antioxidant of the Present Invention]

The antioxidant of the present invention contains a compound selected from the cyclolanostane compound and the lophenol compound as an active ingredient. The compound may be one or more kinds of compounds.

The antioxidant of the present invention preferably contains both a compound selected from the cyclolanostane compound and a compound selected from the lophenol compound in combination. Each of the cyclolanostane compound and the lophenol compound may be one or more kinds of compounds.

In this case, the mass ratio of the cyclolanostane compound and the lophenol compound is preferably within the following range:
cyclolanostane compound:lophenol compound=6.3:2.7 to 5.1:4.9.

The specific mass ratio range almost corresponds to the mass ratio of cyclolanostane compounds (in particular, 9,19-cyclolanostan-3-ol and 24-methylene-9,19-cyclolanostan-3-ol) and lophenol compounds (in particular, 4-methylcholest-7-en-3-ol, 4-methylergost-7-en-3-ol, and 4-methylstigmast-7-en-3-ol) in natural *Aloe barbadensis* Miller.

The concentration of the compound selected from the cyclolanostane compound and the lophenol compound in the antioxidant of the present invention may be appropriately selected depending on a target disease or a subject to be administered. The total concentration is preferably at least 0.0001% by mass, more preferably at least 0.001% by mass, still more preferably at least 0.005% by mass, or particularly preferably at least 0.01% by mass. Further, the upper limit of the total concentration of the compound in the drug of the present invention is not particularly limited, and for example, the concentration is 90% by mass or less, preferably 70% by mass or less, or more preferably 50% by mass or less.

The antioxidant of the present invention may be used in the form of a drug, food or drink, a food additive, an external preparation for skin, or the like.

(Drug of Present Invention)

The antioxidant of the present invention in the form of a drug (referred to as "drug of the present invention") may be administered orally or parenterally to a mammal including a human.

The drug of the present invention can be used for preventing and/or treating a disease or symptom attributed to oxidation of a biological component such as a lipid, in particular, formation of a lipid peroxide. Examples of such disease or symptom include arteriosclerosis, cerebral stroke, angina pectoris, myocardial infarction, hepatic dysfunction, hepatic cirrhosis, hepatitis, retinopathy, cataract, Alzheimer's disease, Parkinson's disease, allergic disease, cancer, skin roughness, aging, atopic dermatitis, and pigmentation such as blotches and freckles, wrinkles and a decrease in elasticity, alopecia, rheumatoid arthritis, Behcet's disease, and other tissue disorders, shoulder stiffness, and excessive sensitivity to cold. Of those, in particular, the drug of the present invention exhibits a remarkable effect on prevention and/or treatment of arteriosclerosis, angina pectoris, and myocardial infarction.

In addition, the drug of the present invention is useful for a person in need of prevention of disease events or reduction of a risk for onset of the events, that is, a person having a risk of an increase in lipid peroxide in a living body.

The dosage form of the drug of the present invention is not particularly limited and may be selected depending on therapeutic purposes or dose regimen. Specific examples thereof include a tablet, a pill, a powder, a liquid, a suspension, an emulsion, a granule, a capsule, a syrup, a suppository, an injection, an ointment, a patch, an ophthalmic solution, and a nasal drop.

The administration time of the drug of the present invention is not particularly limited and may be appropriately selected depending on a target disease. Meanwhile, the dose is preferably determined depending on a dosage form, dose regimen, age and sex of a patient, other conditions, degree of symptom, or the like.

The dose of the drug of the present invention is appropriately selected depending on a dose regimen, age or sex of a patient, degree of the symptom, other conditions, or the like.

Usually, the dose is in the range of preferably 0.001 to 50 mg/kg/day, or more preferably 0.01 to 1 mg/kg/day in terms of the amount of the active ingredient.

Therefore, one of preferred embodiments of the drug of the present invention is a drug which is used such that a compound selected from the cyclolanostane compound and the lophenol compound is administered in a total amount of preferably 0.001 to 50 mg/kg/day, or more preferably 0.01 to 1 mg/kg/day.

The drug of the present invention may contain an additive which is generally used for drugs for inhibiting formation of a lipid peroxide. Examples of the additive include a filler, a binder, a disintegrant, a lubricant, a stabilizer, a flavoring agent, a diluent, a surfactant, and a solvent for injection. Further, the drug of the present invention may contain active ingredients corresponding to diseases or symptoms to be prevented or treated, for example, other ingredients each having an action of improving and/or preventing arteriosclerosis, cerebral stroke, hepatic dysfunction, or the like, as long as the antioxidative activity of the cyclolanostane compound and the lophenol compound is not impaired.

The drug of the present invention can be manufactured by mixing, as an active ingredient, a compound selected from the cyclolanostane compound and the lophenol compound in a carrier for drug. The drug of the present invention can be manufactured by, for example, formulating the above-mentioned compound together with the additive as described above.

Further, the drug of the present invention may be manufactured by formulating an extract, which is obtained by extraction using hot water or another solvent, supercritical extraction, or subcritical extraction using a known plant containing the above-mentioned compound as a raw material, together with the above-mentioned additive.

In particular, the drug of the present invention which contains the cyclolanostane compound and the lophenol compound at a specific mass ratio within the above-mentioned range, may be manufactured by mixing the compounds at a mass ratio within the above-mentioned range. Further, such a drug may be manufactured by a method such as extraction using various solvents, supercritical extraction, or subcritical extraction using a known plant containing a cyclolanostane compound and a lophenol compound or the like as a raw material.

The drug of the present invention may be manufactured by supercritical extraction for powdery *Aloe barbadensis* mesophyll, which is prepared by freeze-drying or hot-air-drying an *Aloe barbadensis* mesophyll (clear gel) part not containing the leaf skin.

In this case, to improve the extraction efficiency of the cyclolanostane compound and the lophenol compound, supercritical propane, supercritical ethylene, supercritical 1,1,1,2-tetrafluoroethane, or the like may be used as an extraction solvent. However, to improve the safety, carbon dioxide is preferably used. In addition, the extraction temperature may be appropriately selected within a temperature range of 28° C. to 120° C. However, to improve the extraction efficiency of the cyclolanostane compound and the lophenol compound, and to decrease the extraction amount of an anthraquinone compound having a laxative property (such as Aloe-emodin), the temperature is within a range of preferably 50 to 69° C., or more preferably 50 to 59° C. The pressure may be appropriately selected within a range of 5.5 to 60 MPa. However, to improve the extraction efficiency of the cyclolanostane compound and the lophenol compound, and to decrease the content of the anthraquinone compound, the pressure is within a range of preferably 15 to 60 Mpa, or more preferably 15 to 24 Mpa. In addition, to improve the extraction efficiency of the cyclolanostane compound and the lophenol compound, an entrainer such as ethanol may be used. However, to decrease the extraction amount of the anthraquinone compound, it is preferable not to use the entrainer.

The drug of the present invention may be used singly or together with an agent for preventing/treating such known disease as described above. If the drug is used together with the agent, the effect of preventing/treating the above-mentioned disease can be enhanced. The agent for preventing/treating the above-mentioned disease to be used together may be contained in the drug of the present invention as an active ingredient, or may be commercialized as a separate agent without adding the agent in the drug of the present invention to provide a kit including the drug and agent to be used in combination.

The drug of the present invention exerts an excellent effect of inhibiting formation of a lipid peroxide because of the antioxidative action of the compound selected from the cyclolanostane compound and the lophenol compound.

(Food or Drink of Present Invention)

In the case where the antioxidant of the present invention is used in the form of food or drink (referred to as "food or drink of the present invention"), the food or drink can be used for reducing the risk of a disease or symptom attributed to oxidation of a biological component such as a lipid, in particular, formation of a lipid peroxide or for preventing such disease or symptom.

The food or drink of the present invention contains a compound selected from the cyclolanostane compound and the lophenol compound as an active ingredient.

In the present invention, the "food or drink" includes not only food or drink which is ingested by a human but also a feed which is ingested by animals other than a human.

The food or drink of the present invention preferably contains both a compound selected from the cyclolanostane compound and a compound selected from the lophenol compound in combination. Each of the cyclolanostane compound and the lophenol compound may be one or more kinds of compounds.

In this case, the mass ratio of the cyclolanostane compound and the lophenol compound is preferably within the following range:

cyclolanostane compound:lophenol compound=6.3:2.7 to 5.1:4.9.

The concentration of the compound selected from the cyclolanostane compound and the lophenol compound in the food or drink of the present invention is appropriately set depending on the form of the food or drink. The total concentration is preferably at least 0.0001% by mass, more preferably at least 0.001% by mass, still more preferably at least 0.005% by mass, or particularly preferably at least 0.01% by mass. The upper limit of the concentration of the compound in the food or drink of the present invention is not particularly limited, and for example, the total concentration is 90% by mass or less, preferably 70% by mass or less, or more preferably 50% by mass or less.

Further, the concentration of the compound selected from the cyclolanostane compound and lophenol compound in the food or drink of the present invention may be set to a total amount suitable for ingestion in the range of 0.001 to 50 mg/kg/day, or more preferably 0.01 to 1 mg/kg/day depending on the form of the food or drink. Therefore, one of preferred embodiments of the food or drink of the present invention is food or drink which is used so that the compound selected from the cyclolanostane compound and lophenol compound may be ingested in a total amount of preferably 0.001 to 50 mg/kg/day, or more preferably 0.01 to 1 mg/kg/day.

The food or drink of the present invention preferably further contains an emulsifier. The emulsifier is not particularly limited as long as it can be used in food. For example, emulsifiers which are approved as food additives in Japan, such as glycerin fatty acid ester, sucrose fatty acid ester, sorbitan fatty acid ester, propylene glycol fatty acid ester, and lecithins, are preferably used.

The food or drink further containing an emulsifier has a high ability to disperse the compound selected from the cyclolanostane compound and lophenol compound and can provide its effect very stably.

Further, if the compound selected from the cyclolanostane compound and lophenol compound may be processed into food or drink containing a fat and oil, or preferably food or drink containing a fat and oil as a major component, it is possible to provide food or drink having excellent storage stability because deterioration due to oxidation of a lipid is inhibited. The content of the above-mentioned compound, or mass ratio of cyclolanostane compound and lophenol compound in the case of mixing these compounds is as mentioned above. Also, such food or drink is preferably emulsified. Examples of the food or drink containing a fat and oil include edible oil, dressing, mayonnaise, butter, margarine, and cream. The emulsified food is preferably contains an emulsifier. Preferred emulsifiers are as mentioned above.

The food or drink of the present invention is preferably a functional food or drink.

The "functional food or drink" means food which directly or indirectly indicates the effect of preventing a disease or the effect of reducing a risk of disease development. Examples thereof include foods which are now sold in Japan as foods for specified health use and health supplements.

Examples of the form of the food or drink of the present invention include drinks such as a soft drink, a carbonated drink, a nutritional drink, a fruit juice drink, and a lactic acid bacteria drink (including concentrated stock solutions of those drinks and powders for preparation of those drinks); ices such as an ice cream, an ice sherbet, and a shaved ice; noodles such as a buckwheat noodle, a wheat noodle, bean-starch vermicelli, a dumpling wrap, a su my wrap, a Chinese noodle, and an instant noodle; confectionery such as a hard candy, a chewing gum, a candy, a gum, chocolate, tablet confectionery, a snack, a biscuit, a jelly, a jam, a cream, and baked confectionery; processed marine and livestock products such as a boiled fish paste, ham, and sausage; dairy products such as processed milk, a milk drink, fermented milk, and butter; a daily dish and bakery; other foods or drinks such as an enteral nutrition food, a fluid diet, milk for infants, and a sport drink.

In particular, the functional food or drink is preferably in the form of a granular, tablet, or liquid supplement because a person who ingests the food can easily recognize the amount of an active ingredient to be ingested.

The food or drink of the present invention preferably has an indication of a purpose such as "for antioxidation," "for inhibiting oxidation of a lipid," or "for inhibiting formation of a lipid peroxide." That is, the food or drink of the present invention is preferably sold as, for example, food or drink for inhibiting formation of a lipid peroxide, which has the indication of the purpose "for inhibiting formation of a lipid peroxide" and contains a compound selected from the cyclolanostane compound and the lophenol compound as an active ingredient.

The "indication" includes all indications which inform consumers about the above-mentioned purposes. That is, the "indication" includes all indications which may remind and evoke anyone of the above-mentioned purposes regardless of indication aims, indication contents, and targets/media to be indicated.

Further, the phrase "has an indication" means an indication action to give recognition of the indication in relation to the food or drink (product).

The indication action is preferably one which gives the above-mentioned purposes directly to consumers. Specific examples thereof include a write-down action of the above-mentioned purposes for a product according to the food or drink of the present invention or a package of the product, an advertisement for the product, and a write-down action of the above-mentioned purposes for a price list or a deal Document (including one supplied by an electromagnetic method).

Meanwhile, the content of the indication (indication content) is preferably one which is approved by the government or the like (for example, an indication which is approved based on various institutions specified by the government and has a form based on the approbation).

Examples thereof include indications on a health food, a functional food or drink, an enteral food, food for special dietary use, food with health claims, food for specified health use, food with nutrient function claims, a quasi drug, and the like. In particular, the indication includes an indication approved by Health, Labour and Welfare Ministry, e.g., an indication approved by the system of food for specified health use or one similar to the system. Examples of the latter include an indication as food for specified health use, an indication as a conditional food for specified health use, an indication showing a possibility of affecting the structure or function of the body, and an indication of a decrease in a disease risk. Specifically, as a typical indication, there are exemplified an indication as food for specified health use specified by the ordinance for health promotion action (the Ordinance No. 86 of Japan Health, Labour and Welfare Ministry, Apr. 30, 2003) (in particular, an indication of a health purpose), and one similar to the indication.

Needless to say, the tenors showing the above-mentioned purposes are not limited to tenors of "for antioxidation," "for inhibiting oxidation of a lipid," and "for inhibiting formation of a lipid peroxide," and a tenor including or an expression which shows an antioxidative action or effect, or an action or effect of inhibiting formation of a lipid peroxide, and a tenor including an expression which relates to an action or effect of preventing a disease or symptom attributed to an ROS or a lipid peroxide, or an action or effect of reducing a risk of onset of the disease or symptom are included in the scope of the present invention. Examples thereof include "(for) a person with a higher level of a lipid peroxide," "for a person with a higher level of lipid peroxide," "(for) a person having a problem in a lipid peroxide level," and "for a person having a problem in a lipid peroxide level."

Further, the food or drink of the present invention preferably includes not only an indication of the above-mentioned purposes but also an indication of the above-mentioned active ingredient and an indication showing the association between the purposes and active ingredient.

The food or drink of the present invention can be manufactured by mixing, as an active ingredient, the compound selected from the cyclolanostane compound and the lophenol compound. The food or drink of the present invention can be manufactured by, for example, mixing the above-mentioned compound with food or drink raw material, and processing the mixture.

Also, the food or drink of the present invention can be manufactured by processing an extract, which is obtained by extraction with hot water or various solvents, supercritical extraction, or subcritical extraction from a known plant or the like as a raw material which contains the above-mentioned compound, together with a food or drink raw material. A specific method of obtaining the extract is as mentioned in the section "Drug of present invention."

Further, in the case where the form of the food or drink of the present invention is a granular, tablet, or liquid supplement, a compound selected from a cyclolanostane compound and a lophenol compound serving as an active ingredient is preferably formulated together with: for example, sugars such as lactulose, maltitol, and lactitol, and other sugars such as dextrin and starch; proteins such as gelatin, soybean protein, and corn protein; amino acids such as alanine, glutamine, and isoleucine; polysaccharides such as cellulose and gum arabic; and fats and oils such as soybean oil and medium-chain triglyceride.

(Food Additive of Present Invention)

In the case where the antioxidant of the present invention is used in the form of a food additive (referred to as "food additive of the present invention"), the food additive, which has been added to food or drink, can be used for reducing the risk of a disease or symptom attributed to oxidation of a biological component such as a lipid, in particular, formation of a lipid peroxide or for preventing such disease or symptom.

Further, the food additive of the present invention may be added to food or drink for inhibiting oxidation of a component in the food or drink, for example, oxidation of a lipid, before use. It is particularly suited that the food additive of the present invention be added to food or drink containing a fat and oil, or preferably food or drink containing a fat and oil as a major component. Examples of the food or drink containing a fat and oil are as listed in the section "Food or drink of present invention."

The food additive of the present invention contains a compound selected from the cyclolanostane compound and the lophenol compound as an active ingredient. The compound may be one or more kinds of compounds.

The food additive of the present invention preferably contains both a compound selected from the cyclolanostane compound and a compound selected from the lophenol compound in combination. Each of the cyclolanostane compound and the lophenol compound may be one or more kinds of compounds.

In this case, the mass ratio of the cyclolanostane compound and the lophenol compound is preferably within the following range:

cyclolanostane compound:lophenol compound=6.3:2.7 to 5.1:4.9.

The total concentration of the compound selected from the cyclolanostane compound and the lophenol compound in the food additive of the present invention is appropriately set. The total concentration is preferably at least 0.001% by mass, more preferably at least 0.01% by mass, still more preferably at least 0.05% by mass, or particularly preferably at least 0.1% by mass. Further, the upper limit of the concentration of the compound in the food additive of the present invention is not particularly limited, and for example, the total concentration is 90% by mass or less, preferably 70% by mass or less, or more preferably 50% by mass or less.

The food additive of the present invention preferably further contains an emulsifier. The emulsifier is not particularly limited as long as it can be used in food. For example, emulsifiers which are approved as food additives in Japan, such as glycerin fatty acid ester, sucrose fatty acid ester, sorbitan fatty acid ester, propylene glycol fatty acid ester, and lecithins, are preferably used.

When an emulsifier is added to the food additive of the present invention, the dispersibility of the compound selected from the cyclolanostane compound and the lophenol compound serving as an active ingredient of the food additive of the present invention in a water-soluble food or drink is improved.

The form of the food additive of the present invention is not particularly limited and may be a form such as a powder, a granule, a tablet, or a liquid, which is generally used in a food additive.

In the case where the food additive of the present invention contains the emulsifier as described above, the food additive particularly preferably has a form of an emulsifier. When the additive has such form, the dispersibility of the compound selected from the cyclolanostane compound and the lophenol compound in a water-soluble food or drink is further improved.

The food additive of the present invention may contain an additive which is generally used, such as a filler, in addition to the cyclolanostane compound and the lophenol compound serving as an active ingredient, and an emulsifier. Also, the food additive of the present invention may contain another known component which is generally used in a food additive.

The food additive of the present invention can be manufactured by mixing a compound selected from the cyclolanostane compound and the lophenol compound as an active ingredient. The food additive of the present invention may be manufactured by, for example, formulating the above-mentioned active ingredient preferably together with the above-mentioned emulsifier, optionally together with the above-mentioned additive or another component.

Also, the food additive of the present invention can be manufactured by formulating an extract, which is obtained by extraction with hot water or various solvents, supercritical extraction, or subcritical extraction from a known plant or the like as a raw material which contains the above-mentioned compound, preferably together with the above-mentioned emulsifier, optionally together with the above-mentioned additive or another component. A specific method of obtaining the extract is as mentioned in the section "Drug of present invention."

The food additive of the present invention may be used for manufacturing the above-mentioned food or drink of the present invention. The amount of the food additive added to food or drink may be appropriately adjusted based on the concentration of the compound selected from the cyclolanostane compound and the lophenol compound serving as an active ingredient in the above-mentioned food or drink of the present invention.

Further, the food additive of the present invention preferably has an indication of a purpose such as "for antioxidation," "for inhibiting oxidation of a lipid," or "for inhibiting formation of a lipid peroxide."

The "indication" and "indication action" are as mentioned in the section "Food or drink of present invention."

(External Preparation for Skin of Present Invention)

The antioxidant of the present invention in the form of an external preparation for skin (referred to as "external preparation for skin of the present invention") can be used for treating or improving, or preventing skin symptoms attributed to oxidation of a biological component such as a lipid, in particular, formation of a lipid peroxide.

For example, the preparation can be used for improving or preventing pigmentation such as blotches or freckles, and dermatitis such as atopic dermatitis or acne, or for improving or preventing wrinkles, a decrease in elasticity, alopecia, and the like.

The external preparation for skin includes all of drugs, quasi drugs, and cosmetics.

The external preparation for skin can be manufactured by mixing the compound represented by the compound selected from the cyclolanostane compound and lophenol compound in a base material which is generally known. The method of extracting the compound or the like is as mentioned in "Drug of present invention."

[Method of Imparting Antioxidative Activity of Present Invention]

The present invention includes a method of imparting, to food or drink, an antioxidative activity, preferably an activity to inhibit oxidation of a lipid, or more preferably an activity to inhibit formation of a lipid peroxide, the method including adding a compound selected from the cyclolanostane compound and lophenol compound to the food or drink so that the concentration of the compound in the food or drink is at least 0.0001% by mass, preferably at least 0.001% by mass, still more preferably at least 0.005% by mass, or particularly preferably at least 0.01% by mass. In this case with regard to the definition of the "food or drink," the definition of the food or drink in the section "Food or drink of present invention" above is applied.

Further, regarding the mixing ratio of the cyclolanostane compound and the lophenol compound, or preferred compounds of these compounds, the description in the section "Food or drink of present invention" above is applied.

The "adding the compound . . . " includes adding a compound obtained by purification or synthesis as well as adding an extract obtained by concentrating the above-mentioned compound by extraction with hot water or various solvents, supercritical extraction, or subcritical extraction from a known plant or the like as a raw material which contains the above-mentioned compound. A specific method of obtaining the extract is as mentioned in the section "Drug of present invention."

[Method of Enhancing Antioxidative Activity of Present Invention]

Further, the present invention includes a method of enhancing an antioxidative activity of food or drink containing a compound selected from the cyclolanostane compound and the lophenol compound, preferably an activity to inhibit oxidation of a lipid, or more preferably an activity to inhibit formation of a lipid peroxide, the method including adding the compound selected from the cyclolanostane compound and the lophenol compound to the food or drink so that the total concentration of the compound in the food or drink is at least 0.0001% by mass, preferably at least 0.001% by mass, still more preferably at least 0.005% by mass, or particularly preferably at least 0.01% by mass. Also in this case, the definition of the "food or drink," the definition of the food or drink in the section "Food or drink of present invention" above is applied.

Further, regarding the mixing ratio of the cyclolanostane compound and the lophenol compound, or preferred compounds of these compounds, the description in the section "Food or drink of present invention" above is applied.

The food or drink containing the compound selected from the cyclolanostane compound and the lophenol compound includes food or drink containing an extract of a Liliaceae plant. Examples thereof include food or drink containing a mesophyll of an Aloe plant. As described above, the "adding the compound . . . " includes adding a compound obtained by purification or synthesis as well as adding the above-mentioned extract.

[Evaluation of Action of Inhibiting Formation of Lipid Peroxide]

The actions of inhibiting formation of a lipid peroxide of various test samples including the antioxidant of the present invention can be evaluated by using, as an index, the amount of a thiobarbituric acid (TBA) reactive substance (TBARS), for example. Specifically, it may be defined that the larger the amount of the TBARS, the larger the amount of a lipid peroxide formed.

Examples of the TEARS include malondialdehyde (MDA) which reacts with TBA under high-temperature and acidic conditions and is a natural by-product of a lipid peroxidation. An MDA-TBA adduct can be detected by measurement of an absorbance at 530 to 540 nm to perform colorimetric measurement of MDA.

Also, the action of inhibiting formation of a lipid peroxide of a test sample can be evaluated using ApoE gene-deficient mice, which are often used as model animals which develop arteriosclerosis by hypercholesterolemia (hyper-LDL-cholesterolemia) (for example, see Reference Document 1: "Saibokogaku (Cell Engineering)," Extra Issue, "Medical Experiment Manual" series, Strategy for Study of Arteriosclerosis+Hyperlipidemia, Shujunsha Co., 1st edition, 1st impression, published on Apr. 1, 1996, pp. 441-443).

The model mice do not exhibit obesity and are known to develop hyper-LDL-cholesterolemia, arteriosclerosis, and cardiovascular diseases in this order. Further, in the model mice, the lipid peroxide level is higher than that of normal mice, and formation of atherosclerotic lesions (plagues) in the artery is observed with time. Therefore, the action of inhibiting formation of a lipid peroxide of a test sample can be evaluated by administering the test sample to the model mice and measuring a lipid peroxide in blood of the model mice.

In addition, it is generally known that a primary lesion of arteriosclerosis is caused by oxidized LDL. Therefore, it is also possible to evaluate the action of reducing a risk of arteriosclerosis through inhibiting formation of a lipid peroxide of the test sample by counting the number of atherosclerotic lesions (plaques) in the artery of each model mouse treated with the test sample.

PRODUCTION EXAMPLE 1

(Production of Cyclolanostane Compound)

To 8.0 g of γ-oryzanol (manufactured by Oryza Oil & Fat Chemical Co., Ltd.) were added 250 ml of distilled water, 50 g of sodium hydroxide, 150 ml of isopropanol, 150 ml of ethanol, and 150 ml of methanol, and the mixture was heated to reflux for 2 hours using a mantle heater. After the reaction, the reaction solution was poured in 1300 ml of water, and white precipitates formed were separated by suction filtration. To wash residual alkali, the separated residue was suspended in 1000 ml of water, followed by suction filtration again. The procedure was repeated twice, and the final residue was freeze-dried under reduced pressure, to thereby obtain 5.91 g of an oryzanol hydrolysate. The hydrolysate was purified by HPLC, to thereby obtain 2435 mg of cycloartenol and 1543 mg of 24-methylene-9,19-cyclolanostan-3-ol.

Subsequently, the resultant cycloartenol was used to synthesize 9,19-cyclolanostan-3-ol. 302 mg of cycloartenol, 150 ml of isopropanol, and 1.0 g of 5% powdery palladium-supported carbon catalyst were fed and sealed in an autoclave, followed by nitrogen gas replacement. Then, hydrogen gas was introduced under a pressure of 3 kg/cm$^2$. The mixture was heated with stirring, and the hydrogen pressure was adjusted to 5 kg/cm² when the temperature reached 50° C. The mixture was allowed to react for 6 hours while the pressure was maintained by compensating for hydrogen absorbed. The reaction solution was filtrated to remove the catalyst, concentrated, and purified by silica gel column chromatography (developing solvent: chloroform 100%), to thereby obtain 275 mg of 9,19-cyclolanostan-3-ol.

PRODUCTION EXAMPLE 2

(Production of Lophenol Compound)

100 kg of mesophyll of *Aloe barbadensis* Miller (clear gel part) were liquefied using a homogenizer, and 100 L of an ethyl acetate/butanol mixed solution (3:1) were added thereto, followed by stirring. The mixture was left to stand overnight and separated into the ethyl acetate/butanol mixed solution and the aqueous layer, followed by collection of the ethyl acetate/butanol mixed solution. The ethyl acetate/butanol mixed solution was concentrated under reduced pressure, to thereby obtain 13.5 g of an extract of the ethyl acetate/butanol mixed solution.

A solution obtained by dissolving 13 g of the extract in 1 ml of a chloroform/methanol mixed solution (1:1) was passed through a column filled with 400 g of silica gel 60 (manufactured by Merck & Co., Inc.) to adsorb to the column, and elution was performed using chloroform/methanol mixed solutions (mixing ratios of chloroform:methanol=100:1, 25:1, 10:1, 5:1, and 1:1) by a stepwise gradient method where the concentration of methanol was increased in a stepwise fashion to fractionate the eluted solutions into fractions with the respective mixing ratios of the mixed solution. Of those fractions, the fraction eluted with chloroform:methanol=25:1 was subjected to normal-phase and reverse-phase thin-layer chromatography (manufactured by Merck & Co., Inc., silica gel 60F254 and RP-18F2543) to confirm that the lophenol compound of the present invention was present in the fraction.

The solvent in the fraction was removed, and the residue was dissolved in a chloroform/methanol mixed solution (1:1). The solution was passed through a column filled with 100 g of silica gel 60 to adsorb to the column, and elution was performed using 1100 ml of a hexane/ethyl acetate mixed solution (4:1). The eluted fractions were divided into fractions of 300 ml (fraction A), 300 ml (fraction B), and 500 ml (fraction C), in this order.

Normal-phase and reverse-phase thin-layer chromatography revealed that the lophenol compound of the present invention was concentrated in the fraction A. The fraction A was further separated with a chloroform/hexane mixed solution (85:15) using HPLC equipped with COSMOSIL C18 (manufactured by Nacalai Tesque, Inc.), to thereby obtain 4-methylcholest-7-en-3-ol, 4-methylergost-7-en-3-ol, and 4-methylstigmast-7-en-3-ol in amounts of 1.3 mg, 1.2 mg, and 1 mg, respectively. The structure of each compound was confirmed by MS and NMR.

PRODUCTION EXAMPLE 3

(Production of Mixture of Cyclolanostane Compound and Lophenol Compound)

The leaf skin of an *Aloe barbadensis* Miller was peeled off to collect the mesophyll part, and the collected mesophyll part was freeze-dried to prepare Aloe vera mesophyll powder. Subsequently, 806 g of the prepared Aloe vera mesophyll powder was fed in an extraction chamber of a supercritical extraction device (4 L) manufactured by Mitsubishi Kakoki Kaisha, Ltd., and extraction was performed for 70 minutes using carbon dioxide under extraction conditions of a temperature of 60° C. and a pressure of 30 MPa. Water was removed from the resultant extract to manufacture 3.58 g of a solid extract.

Identification of the components in the manufactured solid extract revealed that the mass ratio of 9,19-cyclolanostan-3-ol, 24-methylene-9,19-cyclolanostan-3-ol, 4-methylcholest-7-en-3-ol, 4-methylergost-7-en-3-ol, and 4-methylstigmast-7-en-3-ol was 2.8:3.3:1.4:1.5:1.

Therefore, the mass ratio of the cyclolanostane compounds and the lophenol compounds in the mixture of the cyclolanostane compound and the lophenol compounds manufactured in Production Example 3 was found to be as follows: cyclolanostane compound:lophenol compound=6.1:3.9.

PRODUCTION EXAMPLE 4

(Production of Food Additive Containing Mixture of Cyclolanostane Compound and Lophenol Compound)

A food additive containing a mixture of a cyclolanostane compound and a lophenol compound was manufactured by mixing the mixture of the cyclolanostane compounds and the lophenol compounds manufactured in Production Example 3 (4%), medium chain fatty acid (MCT: manufactured by Riken Vitamin Co., Ltd.) (2%), glycerin fatty acid ester (manufactured by Riken Vitamin Co., Ltd.) (4%), saponin (manufactured by Maruzen Pharmaceuticals Co., Ltd.) (0.5%), ethanol (manufactured by Japan Alcohol Corporation) (0.2%), maltitol (manufactured by Hayashibara) (1.3%), glycerin (manufactured by NOF CORPORATION) (78%), and water (10%).

EXAMPLES

Hereinafter, the present invention is described in more detail by way of examples. However, the present invention is not limited to the following examples.

Example 1

Model animals which develop arteriosclerosis, ApoE gene-deficient mice, were used to examine an action of inhibiting formation of a lipid peroxide of a cyclolanostane compound, a lophenol compound, and a mixture of the cyclolanostane compound and the lophenol compound.

(1) Sample Preparation 9,19-Cyclolanostan-3-ol and 24-methylene-9,19-cyclolanostan-3-ol manufactured in Production Example 1 above were used as test sample 1 and test sample 2, respectively.

4-Methylcholest-7-en-3-ol, 4-methylergost-7-en-3-ol, and 4-methylstigmast-7-en-3-ol manufactured in Production Example 2 above were used as test sample 3, test sample 4, and test sample 5, respectively.

The mixture of the cyclolanostane compound and the lophenol compound manufactured in Production Example 3 above (cyclolanostane compound: lophenol compound=6.1:3.9) was used as test sample 6.

Further, Mevalotin (DAIICHI SANKYO COMPANY, LIMITED.), which is an HMG-CoA reductase inhibitor (drug for hyperlipemia), was used as a control sample.

Those samples were separately dissolved in propylene glycol, and diluted with distilled water so as to obtain test solutions with the concentration of each compound of 30 μg/ml, and the solutions were used for a test. Note that physiological saline was used as a negative sample.

(2) Test Method

Six-week-old male ApoE gene-deficient mice (purchased from Japan SLC, Inc.) were preliminarily fed with a high-cholesterol diet (manufactured by Research Diets, Inc.) for 2 weeks and divided into groups each of 15 mice.

To mice of each group, the test solution including the test samples 1 to 6, control sample, or negative sample was separately administered orally once a day for 3 consecutive days using medical probes in an amount of 1 ml per 25 g of mouse body weight. At an early period after the start of administration (14 days after the start of administration), blood was collected from the tail vein of each mouse, and serum was separated. Then, the amount of TBARS was measured using OxiSelect TBARS Assay Kit (manufactured by MDA Quantitation). Meanwhile, as a control, blood was collected from each normal mouse in the same manner as above.

(3) Test Results

Test results of this example are shown in Table 1. Table 1 shows the amount of a lipid peroxide in blood (MDA concentration in serum) in the case where a sample was administered to each mouse in an amount of 30 μg per day.

In the case of the mice treated with the negative sample, the lipid peroxide in blood was found to tend to increase compared with the normal mice. However, in the case of the model mice successively treated with the test samples 1 to 6, the effect of inhibiting formation of a lipid peroxide in blood was clearly confirmed (there is a significant difference, the symbol "*" in the table). The results show that administration of the cyclolanostane compound, the lophenol compound, or the mixture of the cyclolanostane compound and the lophenol compound to the ApoE gene-deficient mice leads to a decrease in the concentration of a lipid peroxide in blood to a level almost equal to that of the normal mice and is effective for preventing or treating arteriosclerosis.

On the other hand, in the case of the mice treated with the control sample, Mevalotin, a significant decrease in amount of a lipid peroxide in blood was not observed compared with the negative sample.

Note that side effects were not observed during administration of the test samples, and there was no abnormality in pathological findings after administration.

The above-mentioned results indicate that the cyclolanostane compound, the lophenol compound, and the mixture of the cyclolanostane compound and the lophenol compound each have the effect of inhibiting formation of a lipid peroxide and is effective for preventing or treating arteriosclerosis.

TABLE 1

| Mouse/sample | | Amount of lipid peroxide in blood (MDA concentration (μM)) | p value |
|---|---|---|---|
| Normal mouse | | $0.5 \pm 0.19$ | — |
| ApoE gene-deficient mice | Test sample 1 | $0.62 \pm 0.01$ | 0.00000002* |
| | Test sample 2 | $0.5 \pm 0.19$ | 0.0001* |
| | Test sample 3 | $0.71 \pm 0.08$ | 0.00003* |
| | Test sample 4 | $0.69 \pm 0.05$ | 0.000002* |
| | Test sample 5 | $0.72 \pm 0.02$ | 0.000003* |
| | Test sample 6 | $0.69 \pm 0.02$ | 0.000003* |
| | Control sample | $0.93 \pm 0.05$ | 0.11 |
| | Negative sample | $0.99 \pm 0.06$ | — |

Example 2

In Example 2, a cyclolanostane compound, a lophenol compound, and a mixture of the cyclolanostane compound and the lophenol compound were each evaluated on the effect of reducing a risk of arteriosclerosis through the effect of inhibiting a lipid peroxide by counting the number of atherosclerotic lesions (plaques) in the artery using known arteriosclerosis model animals, ApoE gene-deficient mice.

(1) Sample Preparation

Test samples 1 to 6, a control sample, and a negative sample were prepared in the same way as in Example 1 above and were each used for a test.

(2) Test Method

Six-week-old male ApoE gene-deficient mice (purchased from Japan SLC, Inc.) were preliminarily fed with a high-cholesterol diet (manufactured by Research Diets, Inc.) for 2 weeks and divided into groups each of 15 mice.

To mice of each group, the sample solution including the test samples, control sample, or negative sample was separately administered orally once a day for 39 consecutive days using medical probes in an amount of 1 ml per 25 g of mouse body weight. Forty days after the start of administration, the thoracic aorta part was fixed with formalin and stained with Oil red, and the number of plaques was counted.

(3) Test Results

The test results of this example are shown in Tale 2. Table 2 shows the numbers of atherosclerotic lesions (plaques) in the arteries of the model mice treated with the sample solutions.

The results revealed that the number of the plaques of the model mice treated with the negative sample was found to be 12.2, while the number of the plaques of the model mice treated with the test samples 1 to 6 was found to decrease by half to 5.0 to 6.2, and the test samples each had an effect of inhibiting plaque formation on the arterial endothelium.

On the other hand, in the case of the mice treated with the control sample, Mevalotin, which is a drug for hyperlipemia, there was no significant difference although plaque formation was found to decrease compared with the negative sample.

Note that during and after administration, no side effects were observed in terms of the body weights and pathological findings of the mice.

The above-mentioned results clarified that the cyclolanostane compound, the lophenol compound, and the mixture of the cyclolanostane compound and the lophenol compound each have an effect of inhibiting plaque formation in the vein and reduced a risk of arteriosclerosis through the effect of inhibiting formation of a lipid peroxide.

TABLE 2

| Mouse/sample | | Number of plaques formed in thoracic aorta | p value |
|---|---|---|---|
| ApoE gene-deficient mice | Test sample 1 | $6.0 \pm 0.7$ | 0.009* |
| | Test sample 2 | $5.6 \pm 1.5$ | 0.0006* |
| | Test sample 3 | $6.2 \pm 1.9$ | 0.008* |
| | Test sample 4 | $5.0 \pm 1.4$ | 0.003* |
| | Test sample 5 | $5.6 \pm 2.1$ | 0.005* |
| | Test sample 6 | $5.4 \pm 2.0$ | 0.004* |
| | Control sample | $10.6 \pm 3.2$ | 0.25 |
| | Negative sample | $12.2 \pm 3.0$ | — |

INDUSTRIAL APPLICABILITY

The antioxidant of the present invention can be administered safely and inhibits oxidation of a biological component, in particular, effectively inhibits formation of a lipid peroxide in blood. Therefore, the antioxidant is effective for treating and/or preventing diseases and symptoms such as arteriosclerosis, cerebral stroke, angina pectoris, myocardial infarction, hepatic dysfunction, hepatic cirrhosis, hepatitis, retinopathy, cataract, Alzheimer's disease, Parkinson's disease, allergic disease, cancer, skin roughness, and aging. Of those, the antioxidant of the present invention has a remarkable effect of treating and/or preventing arteriosclerosis, angina pectoris, and myocardial infarction. Accordingly, the drug of the present invention is useful for treating and preventing the above-mentioned diseases and symptoms. Further, the food or drink of the present invention is useful when ingested for preventing the above-mentioned diseases and symptoms and for reducing a risk of onset thereof because the food or drink can be ingested safely and effectively inhibits formation of a lipid peroxide in a living body, in particular, in blood. In addition, the food additive of the present invention is useful for manufacturing such food or drink and inhibiting oxidation of a component in food or drink. Moreover, the external preparation for skin of the present invention is useful for treating or improving or preventing pigmentation such as blotches or freckles, dermatitis such as atopic dermatitis or acne, or for improving or preventing wrinkles, a decrease in elasticity, alopecia, and the like.

What is claimed is:

1. A method of treating arteriosclerosis, comprising administering a composition containing a cyclolanostane compound and a lophenol compound at the following mass ratio to a subject in need thereof:
 cyclolanostane compound:lophenol compound=6.3:2.7 to 5.1:4.9.

2. The method according to claim 1, wherein the total concentration of the cyclolanostane compound and the lophenol compound is at a concentration of at least 0.0001% by mass.

3. The method according to claim 1 or 2, wherein the cyclolanostane compound is selected from 9,19-cyclolanostan-3-ol and 24-methylene-9,19-cyclolanostan-3-ol.

4. The method according to claim 1 or 2, wherein the lophenol compound is selected from 4-methylcholest-7-en-3-ol, 4-methylergost-7-en-3-ol, and 4-methylstigmast-7-en-3-ol.

5. A method of treating one or more disease or symptom selected from the group consisting of skin roughness, skin aging, atopic dermatitis, blotches, freckles, wrinkles and a decrease in skin elasticity and alopecia, comprising administering a composition containing a cyclolanostane compound and a lophenol compound at the following mass ratio to a subject in need thereof:
 cyclolanostane compound:lophenol compound=6.3:2.7 to 5.1:4.9.

6. The method according to claim 5, wherein the total concentration of the cyclolanostane compound and the lophenol compound is at a concentration of at least 0.0001% by mass.

7. The method according to claim 5 or 6, wherein the cyclolanostane compound is selected from 9,19-cyclolanostan-3-ol and 24-methylene-9,19-cyclolanostan-3-ol.

8. The method according to claim 5 or 6, wherein the lophenol compound is selected from 4-methylcholest-7-en-3-ol, 4-methylergost-7-en-3-ol and 4-methylstigmast-7-en-3-ol.

* * * * *